US012618821B2

(12) United States Patent
Anciaux et al.

(10) Patent No.: US 12,618,821 B2
(45) Date of Patent: May 5, 2026

(54) POWDER COMPOSITION, KIT, AND METHOD FOR DETERMINING ORTHOPHOSPHATE CONCENTRATION

(71) Applicant: HACH COMPANY, Loveland, CO (US)

(72) Inventors: Sarah Anciaux, Fort Collins, CO (US); Melinda Buyck, Nevada, IA (US)

(73) Assignee: HACH COMPANY, Loveland, CO (US)

( * ) Notice: Subject to any disclaimer, the term of this patent is extended or adjusted under 35 U.S.C. 154(b) by 775 days.

(21) Appl. No.: 17/951,558

(22) Filed: Sep. 23, 2022

(65) Prior Publication Data

US 2024/0102984 A1 Mar. 28, 2024

(51) Int. Cl.
| | |
|---|---|
| *B01L 3/00* | (2006.01) |
| *B01F 33/302* | (2022.01) |
| *B01F 33/3033* | (2022.01) |
| *B01L 7/00* | (2006.01) |
| *B33Y 80/00* | (2015.01) |
| *C12M 1/00* | (2006.01) |
| *C12M 1/34* | (2006.01) |
| *C12M 3/00* | (2006.01) |
| *C12M 3/06* | (2006.01) |
| *C12Q 1/6848* | (2018.01) |
| *C12Q 1/686* | (2018.01) |
| *C12Q 1/6874* | (2018.01) |
| *G01N 21/29* | (2006.01) |
| *G01N 21/78* | (2006.01) |
| *G01N 31/22* | (2006.01) |
| *G01N 33/18* | (2006.01) |

(52) U.S. Cl.
CPC ........... *G01N 33/182* (2013.01); *G01N 21/78* (2013.01); *G01N 31/22* (2013.01); *C04B 2235/447* (2013.01)

(58) Field of Classification Search
CPC ...... G01N 33/182; G01N 21/78; G01N 31/22; C04B 2235/447
See application file for complete search history.

(56) References Cited

FOREIGN PATENT DOCUMENTS

| | | | | | |
|---|---|---|---|---|---|
| CN | 102914539 | A | * | 2/2013 | |
| CN | 109142621 | A | * | 1/2019 | ............ G01N 31/22 |
| CN | 113884452 | A | * | 1/2022 | ............ G01N 21/31 |
| KR | 20130115547 | A | * | 10/2013 | ............ G01N 33/18 |
| WO | WO-9400595 | A1 | * | 1/1994 | ............ C23F 11/08 |
| WO | WO-2021257554 | A1 | * | 12/2021 | ............ G01N 31/22 |

OTHER PUBLICATIONS

Spectrum "https://www.spectrumchemical.com/2-hydroxypropyl-beta-cyclodextrin-h2690?srsltid=AfmBOopIERk2EsDJtDTwShnx2si2xL2izxUIICWZ4oClteLTMm8Lhwl2" (Year: 2013).*
Hach "https://bpb-us-w2.wpmucdn.com/sites.broward.edu/dist/3/21/files/2021/01/ps-PHOSVER-3-REAGENT-PILLOWS-hach.pdf" (Year: 2021).*
Oct. 23, 2023 International Search Report issued in PCT Application No. PCT/US23/27821.
Oct. 23, 2023 Written Opinion of the International Searching Authority issued in PCT Application No. PCT/US23/27821.
"Standard Methods for the Examination of Water and Wastewater"; American Public Health Association, American Water Works Association, Water Environment Federation; 1999.

* cited by examiner

*Primary Examiner* — Jennifer Wecker
*Assistant Examiner* — Oyeleye Alexander Alabi
(74) *Attorney, Agent, or Firm* — Oliff PLC

(57) ABSTRACT

A kit and powder composition are described that can be used to determine a concentration of orthophosphate in a water system. The kit includes a first powder composition including molybdate; and a second powder composition including ascorbic acid. A powder composition is also described that includes molybdate, pyrosulfate, and less than 1 wt. % ascorbic acid. A method for determining the concentration of orthophosphate in a water system using the kit includes adding the first and second powder compositions to a water sample collected from the water system, measuring an absorbance of the water sample after the first and second powder compositions have been added to the water sample, and determining the concentration of orthophosphate in the water system based on the measured absorbance.

18 Claims, No Drawings

POWDER COMPOSITION, KIT, AND METHOD FOR DETERMINING ORTHOPHOSPHATE CONCENTRATION

TECHNICAL FIELD

The present disclosure relates to a kit and a powder composition for determining an orthophosphate concentration in a water system, and a method of using the kit to determine the orthophosphate concentration.

BACKGROUND

Phosphates, including orthophosphates, are widely used as corrosion inhibitors in many water systems, such as waste water streams and process streams in various industrial processes. However, when the concentration of orthophosphate is too high, it can cause scaling, fouling, and environmental issues. Therefore, it is important to accurately measure and control the orthophosphate concentration to be within an appropriate range.

A known method for measuring orthophosphate in a water system is the molybdenum blue method (Standard Method 4500-P E, 1997) in which reagents are added to a water sample to react with the orthophosphate in the water sample and produce a blue color having an absorbance proportional to the orthophosphate concentration. A powder composition based on the molybdenum blue method includes molybdate and a reducing agent, such as ascorbic acid. The molybdate reacts with the orthophosphate in the water to produce a heteropoly acid complex, and the reducing agent reduces the complex to produce a blue color. The absorbance of the water sample can then be measured to determine the orthophosphate concentration.

Although the powder composition was originally developed as a stable alternative to reagent solutions, it has long been known that the powder composition can suffer from discoloration during storage, which can result in a loss of chemical function and significantly reduce the accuracy of the measured orthophosphate concentration, as well as cause a poor perception of the powder composition. This problem has plagued the water treatment industry for more than two decades with no known cause or solution. Although there has been speculation as to the source of the problem, for example, that it is caused during the manufacture of one or more of the powder reagents, it has been difficult to determine the source of the problem, which in turn has made it difficult to find an effective solution.

There has been a long felt need for an improved powder composition that can be stably stored without suffering from discoloration and that can be used to accurately measure the orthophosphate concentration in a water system.

SUMMARY

In view of the above, an object of the present disclosure is to provide a stable powder composition and kit that can be used to accurately determine the phosphate concentration.

In one aspect, the disclosure provides a kit including a first powder composition that includes molybdate; and a second powder composition that includes ascorbic acid.

In another aspect, the disclosure provides a powder composition including molybdate, pyrosulfate, and less than 1 wt. % ascorbic acid.

In a further aspect, the disclosure provides a method for determining a concentration of orthophosphate in a water system using the kit. The method includes adding the first powder composition to a water sample collected from the water system, adding the second powder composition to the water sample, measuring an absorbance of the water sample after the first and second powder compositions have been added to the water sample, and determining the concentration of orthophosphate in the water system based on the measured absorbance.

DETAILED DESCRIPTION OF EMBODIMENTS

In the following description, numerous details are set forth to provide an understanding of the present disclosure. However, it may be understood by those skilled in the art that the methods and systems of the present disclosure may be practiced without these details and that numerous variations or modifications from the described embodiments may be possible.

After extensively studying the problem of discoloration, the inventors surprisingly found that discoloration of the powder reagent composition for measuring orthophosphate concentration can be caused by one or more reactions between the reagents under humid conditions. In particular, as shown in the Examples, the inventors found that the ascorbic acid can react with molybdate under humid conditions to produce discoloration in the powder composition. The reaction between ascorbic acid and molybdate produces dark blue or black particles that are insoluble in water and can significantly reduce the accuracy of the orthophosphate concentration measurement. The reaction between ascorbic acid and molybdate in the presence of pyrosulfate produces orange or brown particles that can also interfere with the orthophosphate measurement, as well as cause a poor perception of the powder reagent composition. The inventors found that discoloration can occur in powder compositions that include ascorbic acid and molybdate, and in powder compositions that further include pyrosulfate under humid conditions, for example, at least 50% relative humidity.

The kit and powder compositions disclosed herein can solve the problem of discoloration and provide a stable powder composition for accurately measuring the orthophosphate concentration in water system. For example, in the kit disclosed herein, the ascorbic acid may be provided in a different powder composition from the molybdate. By providing the ascorbic acid separately from the molybdate, discoloration—even when stored under humid conditions—can be eliminated or at least substantially reduced. In another embodiment, a powder composition is provided that includes molybdate, pyrosulfate, and less than 1 wt. % of ascorbic acid. By using a lower amount of ascorbic acid in the powder composition containing molybdate and pyrosulfate, discoloration can be substantially reduced or eliminated even when the powder composition is stored under humid conditions.

The compositions disclosed herein are in a solid form, such as in the form of a dried powder under ambient conditions. Ambient conditions may include a temperature in a range of from 16 to 35° C. and a pressure of 1 atm.

The kit includes a first powder composition including at least molybdate, and a second powder composition including ascorbic acid. The first powder composition and the second powder composition may be separate from each other in the kit. For example, the first powder composition may be provided in a first container, and the second powder composition may be provided in a second container. The first and second containers may be sealed containers, such as powder pillows, sealed plastic bags, vials, test tubes, etc., containing the first and second powder compositions, respectively. The first and second containers can be packaged together in a third larger container (e.g., sealed pouch, box, etc.) and provided as a reagent kit for measuring orthophosphate concentration in water.

The molybdate may be a water-soluble molybdate that can react with orthophosphate to form a phosphomolybdic acid complex under acidic conditions. For example, the molybdate may be sodium molybdate, potassium molybdate, ammonium molybdate, or mixtures thereof. The molybdate is in a solid form, such as in the form of a dried powder. In some embodiments, the molybdate may be present in the first powder composition in an amount in a range of from 0.5 to 20 wt. %, from 0.8 to 10 wt. %, or from 1 to 5 wt. %, based on a total weight of the first powder composition and the second powder composition. Unless stated otherwise, all concentrations (wt. %) disclosed herein with respect to the kit are based on a total weight of the first and second powder compositions.

The first powder composition may also include pyrosulfate. The pyrosulfate may be a water-soluble pyrosulfate that can acidify a water sample. The pyrosulfate may be able to reduce the pH of the water sample to any suitable acidic pH. For example, the pH of the water sample may be reduced to a pH in a range of 0 to 3, a pH in a range of 0.5 to 2.5, or a pH of about 2 or less. The pyrosulfate may be potassium pyrosulfate, sodium pyrosulfate, ammonium pyrosulfate, or mixtures thereof. The pyrosulfate is in a solid form, such as in the form of a dried powder. The pyrosulfate may be present in the first powder composition in an amount in a range of from 50 to 99 wt. %, from 70 to 95 wt. %, or from 75 to 85 wt. %, based on a total weight of the first powder composition and the second powder composition.

The first powder composition may include an acid other than pyrosulfate, either in addition to or in place of the pyrosulfate. The acid may help to reduce the pH of the water sample. The acid may include, for example, powder forms of sulfamic acid, benzenesulfonic acids, trichloroacetic acid, or mixtures thereof. The total amount of the pyrosulfate and other acid(s) when present in the first powder composition may be in a range of from 50 to 99 wt. %, from 70 to 95 wt. %, or from 75 to 85 wt. %, based on a total weight of the first powder composition and the second powder composition. Alternatively, the pyrosulfate and/or the acid other than pyrosulfate may be present in the second powder composition so long as it does not interfere with the performance of the other compounds in the second powder composition.

The first powder composition may include no ascorbic acid, substantially no ascorbic acid, or less than 1 wt. % of ascorbic acid based on a total weight of the first and second powder compositions. As used herein with respect to the kit, "substantially no ascorbic acid" means an ascorbic acid concentration less than 0.01 wt. % based on a total weight of the first and second powder compositions.

The ascorbic acid is provided in a second powder composition different from the first powder composition that includes molybdate. The ascorbic acid is in a solid form, such as in the form of a dried powder, and may be present in the second powder composition in an amount in a range of from 5 to 40 wt. %, from 8 to 30 wt. %, or from 10 to 20 wt. %, based on a total weight of the first powder composition and the second powder composition.

The second powder composition may include no molybdate, substantially no molybdate, or less than 0.5 wt. % of molybdate, based on the total weight of the first and second powder compositions. "Substantially no molybdate" as used herein means less than 0.01 wt. % of molybdate based on the total weight of the first and second powder compositions.

The first and/or second powder composition may further include antimony. The antimony may be a water-soluble antimony. The antimony may be able to accelerate the color formation reaction between the molybdate and the orthophosphate present in the water sample. For example, the antimony may be an alkali metal salt of an antimonyl carboxylate, such as a salt of one or more of antimonyl tartrate, antimonyl glycolate, antimonyl citrate, antimonyl lactate, and antimonyl malate. The alkali metal may be sodium, potassium, rubidium, caesium, lithium, or francium. In one embodiment, the antimony may be potassium antimonyl tartrate. The antimony is in a solid form, such as in the form of a dried powder. The antimony may be present in an amount in a range of from 0.001 to 5 wt. %, from 0.01 to 2 wt. %, or from 0.05 to 0.5 wt. %, based on a total weight of the first powder composition and the second powder composition.

The first and/or second powder composition may further include a chelating agent. The chelating agent can chelate metals which cause instability of the ascorbic acid, or which are otherwise compatible with the other elements present in the kit disclosed herein. For example, the chelating agent may be able to bind to heavy metals capable of catalyzing the decomposition of the ascorbic acid. The chelating agent may be hydroxy carboxylic acid salt and amino carboxylic acid salts, citric acid, phosphonobutane tricarboxylic acid, ethylenediaminetetraacetic acid (EDTA), and nitrilotriacetic acid. EDTA may be used in any of its various salt forms, for example, disodium EDTA, tetrasodium EDTA, edetate sodium, edetate disodium, edetate trisodium, and edetate calcium disodium. The chelating agent is in a solid form, such as in the form of a dried powder. The chelating agent may be present in an amount in a range of from 0.01 to 5 wt. %, from 0.03 to 2 wt. %, or from 0.1 wt. % to 1 wt. %, based on a total weight of the first powder composition and the second powder composition.

In one aspect, the first powder composition includes molybdate, pyrosulfate, a chelating agent, such as EDTA, and antimony, and the second powder composition includes ascorbic acid. By separating the ascorbic acid from the molybdate, the reaction between ascorbic acid and molybdate, either alone or in the presence of pyrosulfate, under humid conditions can be prevented, thereby preventing discoloration and loss of chemical function of the first and second powder compositions. As a result, the first and second powder compositions can be used to accurately measure the orthophosphate concentration in a water sample collected from a water system, as discussed below.

In another embodiment, a powder composition is provided. The powder composition includes molybdate, pyrosulfate, and less than 1 wt. % of ascorbic acid. The powder composition may include less than 0.5 wt. % ascorbic acid, substantially no ascorbic acid, or no ascorbic acid. As used herein with respect to the powder composition, "substantially no ascorbic acid" means that the composition contains less than 0.01 wt. % of ascorbic acid based on a total weight of the powder composition. By using a lower amount of ascorbic acid in the powder composition containing molybdate and pyrosulfate, discoloration can be substantially reduced or eliminated even when the powder composition is stored under humid conditions.

The molybdate and pyrosulfate can be any suitable molybdate and pyrosulfate, such as those discussed above with respect to the kit. The molybdate may be present in the powder composition in an amount in a range of from 0.5 to 20 wt. %, from 1 to 10 wt. %, or from 1.5 to 5 wt. %, based on a total weight of the powder composition. The pyrosulfate may be present in the powder composition in an amount in a range of from 70 to 99.5 wt. %, from 80 to 98.5 wt. %, or from 90 to 98 wt. %, based on a total weight of the powder composition.

The powder composition may further include antimony and/or a chelating agent in the same manner discussed above with respect to the kit. The antimony may be present in the powder composition in an amount in a range of from 0.001 to 5 wt. %, from 0.01 to 2 wt. %, or from 0.05 to 0.5 wt. %, based on a total weight of the powder composition. The chelating agent may be present in the powder composition in an amount in a range of from 0.01 to 5 wt. %, from 0.03 to 2 wt. %, or from 0.1 wt. % to 1 wt. %, based on a total weight of the powder composition.

The powder composition may include less than 0.1 wt. % of vanadate, substantially no vanadate, or no vanadate. As used herein, "substantially no vanadate" means less than 0.01 wt. % of vanadate based on a total weight of the powder composition.

The kit and powder compositions disclosed herein can be used to quickly and accurately determine the concentration of orthophosphate contained in a water system. The powder compositions are stable for long term storage and do not suffer from discoloration and loss of chemical function even when stored under humid conditions. For example, the powder composition may show substantially no discoloration when stored under humid conditions, such as 50% relative humidity or higher, 70% relative humidity or higher, or 90% relative humidity or higher for a duration of at least 1 month, at least 4 months, at least 8 months, or at least 12 months. Thus, the powder compositions can be stored for these periods in a variety of conditions without any observable discoloration.

In another embodiment, a method for determining the concentration of orthophosphate in a water system using the kit is provided. The method may include collecting a water sample from a water system, and adding the first powder composition and the second powder composition to the water sample. For example, a water sample in an amount in a range of from 1 to 50 ml, from 2 to 20 ml, or 5 to 10 ml may be collected in a test tube or vial, and the first and second powder compositions may be added to the sample. The first and second powder compositions may be added in any order. For example, the first powder composition may be added to the water sample first, followed by the second powder composition, or vice versa. Alternatively, the first and second powder compositions may be added to the water sample at the same time. Once the first and second powder compositions have been added, the test tube or vial may be shaken or otherwise mixed for at least 10 seconds, at least 20 seconds, at least 1 minute, and no more than 5 minutes or no more than 2 minutes.

The first powder composition can react with orthophosphate in the water sample to produce a phosphomolybdic acid complex, and the phosphomolybdic acid complex can be reduced by the second powder composition to a molybdenum blue. In particular, the molybdate reacts with the orthophosphate in the water sample under the acidic conditions created by the pyrosulfate and/or other acid to generate a phosphomolybdic acid complex. The complex may also include antimony when present. The antimony is believed to accelerate the reaction between the molybdate and the orthophosphate in the water sample. The phosphomolybdic acid complex is then reduced by the ascorbic acid in the second powder composition to an intensely colored molybdenum blue. The blue-colored water sample has an absorbance proportional to the orthophosphate concentration.

The method further includes measuring an absorbance of the water sample after the first and second powder compositions have been added to the water sample. The absorbance of the water sample can be measured at a wavelength in a range of from 600 to 900 nm, from 610 to 880 nm, or from 625 to 750, for example. The absorbance can be measured using, for example, a spectrophotometer, colorimeter, or any other known instrument suitable for measuring absorbance. The orthophosphate concentration in the water system can be determined colorimetrically from the measured absorbance.

For example, the orthophosphate concentration can be determined by comparing the measured absorbance with a calibration curve obtained in advance by known methods. For example, the calibration curve can be obtained by measuring the absorbance of multiple standard solutions of equal volume having different known concentrations of orthophosphate. Based on the measured absorbance values at different orthophosphate concentrations, a curve of absorbance versus orthophosphate concentration can be plotted to create the calibration curve. The calibration curve can then be used to determine the orthophosphate concentration of water samples containing an unknown amount of orthophosphate by comparing the measured absorbance of the water sample with the calibration curve.

Alternatively, the spectrophotometer, colorimeter, or other instrument for measuring the absorbance may be programmed so as to automatically determine the orthophosphate concentration based on the measured absorbance value using, for example, a calibration curve that has been saved in a memory of the instrument.

The water system tested using the kit and powder compositions disclosed herein may be a water system including less than 20 mg/L orthophosphate, or an orthophosphate concentration in a range of from 0.001 mg/L to 10 mg/L, from 0.01 to 7 mg/L, or 0.06 to 5 mg/L.

The foregoing is further illustrated by reference to the following examples, which are presented for purposes of illustration and are not intended to limit the scope of the present disclosure.

EXAMPLES

Example 1—Reaction Between Ascorbic Acid and Molybdate Under Humid Conditions

Four powder compositions (samples A, B, C, and D) were prepared as shown in Table 1. Samples A and B had the same powder composition including sodium molybdate and ascorbic acid. Sample A was placed in 100% relative humidity for one day, whereas Sample B was stored at room humidity (~35%) for one day. Sample C included molybdate, pyrosulfate, antimony, and EDTA, but did not include ascorbic acid. Sample D included the same powder composition as Sample C except that it also included ascorbic acid. Both samples C and D were placed in 100% humidity for one day. Prior to storage, each composition in samples A, B, C, and D had a white powder appearance.

TABLE 1

| Sample | Powder Composition | Storage Humidity | Appearance After Storage |
|---|---|---|---|
| A | Sodium molybdate Ascorbic acid | 100% | Dark blue/ black powder |
| B | Sodium molybdate Ascorbic acid | Room Humidity | White powder |

TABLE 1-continued

| Sample | Powder Composition | Storage Humidity | Appearance After Storage |
|---|---|---|---|
| C | Sodium molybdate Potassium pyrosulfate Potassium antimonyl tartrate EDTA | 100% | White powder |
| D | Sodium molybdate Potassium pyrosulfate Potassium antimonyl tartrate EDTA Ascorbic acid | 100% | White powder with dark blue/black specks |

As shown in Table 1, when the powder composition included both molybdate and ascorbic acid and was placed in 100% relative humidity for one day as in Samples A and D, dark blue/black particles that are insoluble in water were formed. In Sample A, which only included ascorbic acid and molybdate, the entire powder turned a dark blue/black. In Sample D, which additionally included pyrosulfate, tartrate, and EDTA, dark blue/black specks were created in the white powder. On the other hand, when molybdate and ascorbic acid were stored at room humidity for one day in Sample B, there was no discoloration. Similarly, when the powder composition of Sample C, which included molybdate, but did not include ascorbic acid, was placed in 100% relative humidity for one day, there was no discoloration. The above example shows that ascorbic acid reacts with molybdate under humid conditions, creating a dark blue/black insoluble powder.

Example 2—Reaction Between Ascorbic Acid, Molybdate, and Pyrosulfate Under Humid Conditions Four pairs of samples were prepared as shown in Table 2 below. The two samples (1) and (2) in the respective pairs A, B, C, and D contained the same powder composition. Each pair A, B, C, and D included potassium pyrosulfate and sodium molybdate. Pairs A, B, and C further included: (A) potassium antimonyl tartrate, (B) ascorbic acid, and (C) EDTA. Pair D was a control and only included potassium pyrosulfate and sodium molybdate. Sample (1) of each of the four pairs A, B, C, and D was left at room humidity (approximately 35% relative humidity) for three days, and sample (2) of each of the four pairs A, B, C, and D was placed in a 100% humidity chamber for three days. Prior to storage, the composition in each sample of pairs A, B, C, and D had a white powder appearance.

TABLE 2

| | Sample # | Powder Composition | Storage Humidity | Appearance After Storage |
|---|---|---|---|---|
| Pair A | (1) | Potassium pyrosulfate/Sodium Molybdate Potassium antimonyl tartrate | Room Humidity | White powder |
| | (2) | Potassium pyrosulfate/Sodium Molybdate Potassium antimonyl tartrate | 100% | White powder |
| Pair B | (1) | Potassium pyrosulfate/Sodium Molybdate Ascorbic acid | Room Humidity | White powder |
| | (2) | Potassium pyrosulfate/Sodium Molybdate Ascorbic acid | 100% | Dark sand/brown powder with some black specks |
| Pair C | (1) | Potassium pyrosulfate/Sodium Molybdate EDTA | Room Humidity | White powder |
| | (2) | Potassium pyrosulfate/Sodium Molybdate EDTA | 100% | White powder |
| Pair D | (1) | Potassium pyrosulfate/Sodium Molybdate | Room Humidity | White powder |
| | (2) | Potassium pyrosulfate/Sodium Molybdate | 100% | White powder |

As shown in Table 2, the powder compositions of pairs A, C, and D all had the same appearance after storage at room humidity or at 100% relative humidity after three days. However, in pair B, the powder composition including sodium molybdate, potassium pyrosulfate, and ascorbic acid turned a dark sand/brown color with some black specks after storage at 100% relative humidity for three days. The same powder composition in the first sample in pair B showed no change in appearance after storage at room humidity. The above examples show that ascorbic acid reacts with sodium molybdate in the presence of pyrosulfate under humid conditions, causing discoloration to a dark sand/brown color including black specks.

Example 3—Two Powder Composition System Showed No Discoloration

A first powder composition including potassium pyrosulfate, potassium antimonyl tartrate, EDTA, and sodium molybdate, and a second powder composition including ascorbic acid were prepared, as shown in Table 3 below.

The first and second powder compositions were sealed in separate containers known as powder pillows. A pin hole was punched into each of the powder pillows, and the powder pillows were stored at 97% relative humidity for five days. As shown in Table 3, the first and second powder compositions remained a white color and did not show any discoloration after being stored at 97% relative humidity for five days. This example shows that by separating ascorbic acid from molybdate, discoloration can be avoided.

Comparative Example 1—Single Powder Composition Showed Discoloration

A single powder composition including the same amounts of potassium pyrosulfate, potassium antimonyl tartrate, EDTA, sodium molybdate, and ascorbic acid as in the two powder compositions of Example 3 was prepared and stored in a single powder pillow. A pin hole was punched into the powder pillow, and it was stored at 97% relative humidity for five days.

In contrast to Example 3, the single powder composition of Comparative Example 1 turned a brown mottled black color after being stored at 97% relative humidity, as shown in Table 3 below.

Example 3 and Comparative Example 1 show that by using the two powder system disclosed herein, the reactions between the ascorbic acid and molybdate, either by itself or in the presence of pyrosulfate, under humid conditions, and the resulting discoloration and loss of chemical function that occur in the one powder system, can be prevented.

TABLE 3

| | Powder Composition | | Appearance Before Storage | Appearance After Storage at 97% relative humidity for 5 Days |
|---|---|---|---|---|
| Example 3 | First Powder Composition | Potassium pyrosulfate Postassium antimonyl tartrate EDTA Sodium molybdate | White powder | White powder |
| | Second Powder Composition | Ascorbic acid | White powder | White powder |
| Comparative Example 1 | Single Powder Composition | Potassium pyrosulfate Postassium antimonyl tartrate EDTA Sodium molybdate Ascorbic acid | White powder | Brown mottled black powder |

Example 4—Measuring Orthophosphate Concentration Using a Two Powder System

The first and second powder compositions of Example 3 were used to determine the orthophosphate concentration in a standard solution containing 5 mg/L orthophosphate. 5 ml of the 5 mg/L $PO_4^{3-}$ standard solution was added to a test tube. The first and second powder compositions of Example 3 were added the standard solution in the test tube. Then, the cap was secured on the test tube, and the vial was shaken for at least 20 seconds, after which the solution turned a blue color. After about two minutes, the vial was inserted into a spectrophotometer and the absorbance was measured at a wavelength of 880 nm to determine the orthophosphate concentration using a preprogrammed method correlating the measured absorbance with the orthophosphate concentration. This was repeated several times. The results are shown in Table 4 below.

Reference Example 1—Measuring Orthophosphate Concentration Using Single Powder System A Phos Ver® 3 reagent powder pillow, made by Hach Company, which is a known composition for measuring orthophosphate concentration via the ascorbic acid method, was obtained and used as a control. The single powder composition of the PhosVer® 3 reagent powder pillow was added to a test tube including 5 ml of a 5 mg/L $PO_4^{3-}$ standard solution and used to measure the orthophosphate concentration in the same manner as described in Example 4 above. The results of Example 4 and Reference Example 1 are shown in Table 4 below.

TABLE 4

| | Rep | Orthophosphate concentration (mg/l) |
|---|---|---|
| Example 4 - two powder system | 1 | 5.11 |
| | 2 | 4.95 |
| | 3 | 5.07 |
| | 4 | 4.99 |
| | 5 | 5.06 |
| | 6 | 5.06 |
| | 7 | 4.96 |
| Reference Example 1 - single powder system | 1 | 5.01 |
| | 2 | 5.07 |
| | 3 | 5.13 |
| | 4 | 5.04 |
| | 5 | 5.10 |

TABLE 4-continued

| | Rep | Orthophosphate concentration (mg/l) |
|---|---|---|
| | 6 | 5.00 |
| | 7 | 4.99 |
| Example 4 - two powder system | Average | 5.03 |
| Reference Example 1 - single powder system | Average | 5.05 |
| Example 4 - two powder system | Stdev | 0.061 |
| Reference Example 1 - single powder system | Stdev | 0.053 |
| Example 4 versus Reference Example 1 | % diff | −0.396 |

As shown in Table 4 above, the two powder system obtained substantially the same orthophosphate measurements as the known single powder system. Therefore, the two powder system can be used to accurately measure the orthophosphate concentration.

The two powder system of Example 4 and the single powder system of Reference Example 1 were then stored at room humidity (~35%) for four months. At various times during the four months, the powder compositions of Example 4 and Reference Example 1 were used to determine the orthophosphate concentration of a 5 mg/L $PO_4^{3-}$ standard solution in the same manner described above. The results are shown in Table 5 below.

TABLE 5

| | | Orthophosphate concentration (mg/l) | | | | | |
|---|---|---|---|---|---|---|---|
| | | Month 1 | | 2 | | 3 | 4 |
| | Rep | Day 0 | 14 | 28 | 58 | 72 | 98 |
| Example 4 - two | 1 | 5.11 | 5.05 | 5.10 | 4.98 | 5.02 | 5.07 |
| powder system | 2 | 4.95 | 5.03 | 5.09 | 4.97 | 5.06 | 5.08 |
| | 3 | 5.07 | 4.97 | 4.95 | 4.97 | 5.12 | 5.10 |
| | 4 | 4.99 | | | | | |
| | 5 | 5.06 | | | | | |
| | 6 | 5.06 | | | | | |
| | 7 | 4.96 | | | | | |
| Reference Example 1 - | 1 | 5.01 | 5.00 | 4.99 | 4.96 | 5.10 | 5.11 |
| single powder system | 2 | 5.07 | 5.00 | 4.98 | 5.06 | 5.14 | 5.10 |
| | 3 | 5.13 | 5.04 | 5.11 | 5.03 | 5.15 | 5.06 |
| | 4 | 5.04 | | | | | |
| | 5 | 5.10 | | | | | |
| | 6 | 5.00 | | | | | |
| | 7 | 4.99 | | | | | |
| Example 4 - two powder system | Average | 5.03 | 5.02 | 5.05 | 4.97 | 5.07 | 5.08 |
| Reference Example 1 - single powder system | Average | 5.05 | 5.01 | 5.03 | 5.02 | 5.13 | 5.09 |
| Example 4 - two powder system | Stdev | 0.061 | 0.042 | 0.084 | 0.006 | 0.050 | 0.015 |
| Reference Example 1 - single powder system | Stdev | 0.053 | 0.023 | 0.072 | 0.051 | 0.026 | 0.026 |
| Example 4 - two powder system | % Change | 0.000 | 0.237 | −0.360 | 1.098 | −0.758 | −1.089 |
| Example 4 vs Reference Example 1 | % diff | −0.398 | 0.066 | 0.396 | −0.871 | −1.250 | −0.131 |

As shown in Table 5 above, the two powder system was able to be stably stored for four months without loss of chemical function, and performed equally well to the current single powder composition.

The above Examples show that the two powder system disclosed herein can be used to accurately measure the orthophosphate concentration and unlike the current single powder system, the two powder system can be stably stored—even under humid conditions—without suffering from discoloration and loss of chemical function.

Comparative Example 2

The single powder composition of Comparative Example 1, which had turned a brown mottled black color after being stored at 97% relative humidity, was then used to measure the orthophosphate concentration in a 5 mg/L $PO_4^{3-}$ standard solution in the same manner described in Example 4 above. The discolored powder composition measured an orthophosphate concentration of only 3.5 mg/L in the 5 mg/L $PO_4^{3-}$ standard solution. This Example shows that the reactions under humid conditions not only result in discoloration, but also in loss of chemical function, rendering the powder composition unable to accurately measure the orthophosphate concentration.

Comparative Example 3

Single powder compositions (samples 1-4) including the same compounds as Comparative Example 1 were prepared with decreasing amounts of ascorbic acid, as shown in Table 6 below. The powder composition of Sample 1 had the same composition as Comparative Example 1 such that the amount of ascorbic acid (approximately 17 wt. %) in Sample 1 corresponds to a formulary percent of ascorbic acid of 100%, and Samples 2-4 included decreasing amounts of ascorbic acid, as shown in Table 6 below. The samples were placed in 100% relative humidity for 48 hours.

Each of the samples was then added to a 5 ppm $PO_4^{3-}$ standard solution and the orthophosphate concentration was measured in the same manner described in Example 4 above. As shown in Table 6 below, all of the samples showed discoloration and loss of chemical function after being stored at 100% relative humidity for 48 hours. None of the samples were able to accurately measure the orthophosphate concentration in the 5 ppm $PO_4^{3-}$ standard solution.

TABLE 6

| Sample # | Formulary percent of ascorbic acid | Measured orthophosphate concentration (ppm) in 5 ppm $PO_4^{3-}$ standard solution | Color at 48 hours |
|---|---|---|---|
| 1 | 100% | 0.22 | Brown mottled black |
| 2 | 70% | 0.23 | Brown mottled black |
| 3 | 30% | 0.21 | Brown mottled black |
| 4 | 1.20% | 0.56 | Brown mottled black |

The above example shows that even a small amount of ascorbic acid in combination with molybdate in the presence of pyrosulfate can react when exposed to humid conditions, resulting in discoloration and loss of chemical function, rendering the powder composition ineffective for accurately measuring the orthophosphate concentration.

Although some embodiments of the invention have been described in detail above, those skilled in the art will readily appreciate that many modifications are possible in the example embodiments without materially departing from the disclosed embodiments. Accordingly, all such modifications are intended to be included within the scope of this disclosure as defined in the following claims.

What is claimed is:

1. A kit comprising:
a first powder composition comprising molybdate; and
a second powder composition comprising ascorbic acid,
wherein the first powder composition and the second powder composition are separated from each other, and
wherein the first powder composition and the second powder composition show substantially no discoloration when stored at 50% humidity or higher for at least 4 months.

2. The kit according to claim 1, wherein the first powder composition includes molybdate in an amount in a range of 0.5 to 20 wt. % based on a total weight of the first powder composition and the second powder composition.

3. The kit according to claim 1, wherein the molybdate is selected from the group consisting of sodium molybdate, potassium molybdate, ammonium molybdate, and mixtures thereof.

4. The kit according to claim 1, wherein the first powder composition further includes pyrosulfate.

5. The kit according to claim 4, wherein the pyrosulfate is selected from the group consisting of potassium pyrosulfate, sodium pyrosulfate, ammonium pyrosulfate, and mixtures thereof.

6. The kit according to claim 4, wherein the pyrosulfate is present in the first powder composition in an amount in a range of 50 to 95 wt. % based on a total weight of the first powder composition and the second powder composition.

7. The kit according to claim 1, wherein the first powder composition further includes antimony.

8. The kit according to claim 7, wherein the antimony is potassium antimonyl tartrate.

9. The kit according to claim 1, wherein the first powder composition further includes a chelating agent.

10. The kit according to claim 1, wherein the first powder composition includes:
pyrosulfate in an amount of in a range of 50 to 95 wt. %;
molybdate in an amount in a range of 0.5 to 20 wt. %;
antimony in an amount in a range of 0.01 to 5 wt. %; and a chelating agent in an amount in a range of 0.03 to 5 wt. %, based on a total weight of the first powder composition and the second powder composition.

11. The kit according to claim 1, wherein the ascorbic acid is present in the second powder composition in an amount in a range of 5 to 40 wt. % based on a total weight of the first powder composition and the second powder composition.

12. The kit according to claim 1, wherein the first powder composition is in a first container and the second powder composition is in a second container.

13. A powder composition comprising:
molybdate; and
pyrosulfate;
wherein the powder composition comprises less than 0.01 wt. % of ascorbic acid based on a total weight of the powder composition, and
wherein the pox der composition shows substantially no discoloration when stored at 50% humidity or higher for at least 4 months.

14. The powder composition according to claim 13, further comprising antimony.

15. A method for determining a concentration of orthophosphate in a water system using the kit according to claim 1, the method comprising:
adding the first powder composition to a water sample collected from the water system;
adding the second powder composition to the water sample; and
measuring an absorbance of the water sample after the first powder composition and the second powder composition have been added to the water sample.

16. The method according to claim 15, wherein the first powder composition reacts with orthophosphate in the water sample to produce a phosphomolybdic acid complex, and the phosphomolybdic acid complex is reduced by the second powder composition to a molybdenum blue.

17. The kit according to claim 1, wherein the first powder composition and the second powder composition do not suffer a loss of chemical function when stored at 50% humidity or higher for at least 4 months.

18. The powder composition according to claim 13, wherein the powder composition does not suffer a loss of chemical function when stored at 50% humidity or higher for at least 4 months.

* * * * *